US007883874B2

(12) United States Patent
Gibson et al.

(10) Patent No.: US 7,883,874 B2
(45) Date of Patent: Feb. 8, 2011

(54) GALACTOOLIGOSACCHARIDE COMPOSITION AND THE PREPARATION THEREOF

(75) Inventors: Glenn Gibson, Berkshire (GB); Jacek Witold Slupinski, Kwazulu Natal (ZA); Georgios Tzortzis, Berkshire (GB); Anthony Graham Wynne, Devon (GB)

(73) Assignee: Clasado Inc., Panama (PA)

( * ) Notice: Subject to any disclaimer, the term of this patent is extended or adjusted under 35 U.S.C. 154(b) by 616 days.

(21) Appl. No.: 10/552,483

(22) PCT Filed: Jun. 30, 2004

(86) PCT No.: PCT/GB2004/002815

§ 371 (c)(1),
(2), (4) Date: Apr. 4, 2007

(87) PCT Pub. No.: WO2005/003329

PCT Pub. Date: Jan. 13, 2005

(65) Prior Publication Data

US 2007/0274955 A1    Nov. 29, 2007

(30) Foreign Application Priority Data

| Jun. 30, 2003 | (GB) | ................... | 0315266.7 |
| Oct. 29, 2003 | (GB) | ................... | 0325224.4 |
| Mar. 16, 2004 | (GB) | ................... | 0405837.6 |

(51) Int. Cl.
*C12P 19/04* (2006.01)
(52) U.S. Cl. .............. 435/101; 435/170; 435/252.1
(58) Field of Classification Search ................. 435/101, 435/170, 252.1
See application file for complete search history.

(56) References Cited

U.S. PATENT DOCUMENTS

| 4,435,389 A | 3/1984 | Mutai et al. |
| 4,944,952 A | 7/1990 | Kobayashi et al. |
| 5,149,640 A | 9/1992 | Oonishi et al. |
| 5,294,546 A | 3/1994 | Dombou et al. |
| 2002/0086358 A1* | 7/2002 | Jorgensen et al. .......... 435/69.1 |
| 2004/0131659 A1* | 7/2004 | Gibson et al. ............... 424/439 |

FOREIGN PATENT DOCUMENTS

| EP | 0 438 182 | 7/1991 |
| EP | 1 227 152 A1 | 7/2002 |
| JP | 62059290 | 3/1987 |
| JP | 3049692 | 3/1991 |
| JP | 3049693 | 3/1991 |
| JP | 3246296 | 11/1991 |
| JP | 5-146273 | 6/1993 |
| JP | 05-146296 | 6/1993 |
| JP | 7089976 | 4/1995 |
| JP | 9121853 | 5/1997 |
| JP | 10023898 | 1/1998 |
| WO | WO 88/08025 | 10/1988 |
| WO | WO 96/06924 | 3/1996 |
| WO | WO 0033854 A1 * | 6/2000 |
| WO | WO 00/46345 | 8/2000 |
| WO | WO0190317 | 11/2001 |
| WO | WO 2004/074496 A1 | 9/2004 |

OTHER PUBLICATIONS

Dumortier, V et al. Primary structure of ten galactosides formed by transglycosylation during lactose hydrolysis by *Bifidobacterium bifidum*. Carbohydrate Research. 1990. 201: 115-123.*
Gopal, P.K., et al., "Utilisation of galacto-oligosaccharides as selective substrates for growth by lactic acid bacteria including *Bifidobacterium lactis* DR 10 and *Lactobacillus rhamnosus* DR20," International Dairy Journal 11 (2001) pp. 19-25.
Ziggers, D., "TOS, a new prebiotic derived from whey," FEED MIX, vol. 9, No. 6, 2001, pp. 7-9.
Japanese Office Action dated Dec. 9, 2008, in corresponding Japanese Patent Application No. 2006-500267, along with English translation, indicating the relevance of the cited references in the IDS filed Feb. 24, 2009.
Bouquelet, S et al., Primary Structure of Ten Galactosides formed by Transglycosylation During Lactose Hydrolysis by *Bifidobacterium bifidum*, Carbohydrate Research, vol. 201, 1990 pp. 115-123 (On Order).
Blakeney, A.,et al., A Simple and Rapid Preparation of Alditol Acetates for Monosaccharide Analysis, Carbohydrate Research, Elsevier Scientific Publishing Co., vol. 113 (1983) pp. 291-299.
Gibson, G., et al., Dietary Modulation of the Human Colonic Microbiota: Introducing the Concept of Prebiotics, Critical Review, American Institute of Nutrition, 1995, pp. 1401-1412.
MacFarlane, G., et al., Validation of a Three-Stage Compound Continuous Culture System for Investigating the Effect of Retention Time on the Ecology and Metabolism of Bacteria in the Human Colon, Microbial Ecology, 1998, 35:180-187.
Ciucanu, I., et al., A Simple and Rapid Method for the Permethylation of Carbohydrates, Carbohydrate Research, 131 (1984) pp. 209-217, Elsevier Science Publishers.
MacCormick, C.A., et al., Characterization of a Variant of the Polysaccharide Acetan Produced by a Mutant of *Acetobacter xylinum* Strain CR1/4, Journal of Applied Bacteriology 1993, 74, pp. 196-199.
Doares, Steven, et al., An Improved Method for the Preparation of Standards for Glycosyl-linkage Analysis of Complex Carbohydrates, Carbohydrate Research, 210 (1991) pp. 311-317, Elsevier Science Publishers.

(Continued)

*Primary Examiner*—Leon B. Lankford, Jr.
*Assistant Examiner*—Susan E. Fernandez
(74) *Attorney, Agent, or Firm*—Christie, Parker & Hale, LLP

(57) ABSTRACT

Novel strains of *Bifidobacterium bifidum* capable of producing a novel galactosidase enzyme activity that converts lactose to a novel mixture of galactooligosaccharides. The mixture of oligosaccharides may be incorporated into numerous food products or animal feeds for improving gut health by promoting the growth of bifidobacteria in the gut, and repressing the growth of the pathogenic microflora.

16 Claims, 1 Drawing Sheet

OTHER PUBLICATIONS

Sweet, David, et al., Quantitative Analysis by Various G.L.C. Response-Factor Theories for Partially Methylated and Partially Ethylated Alditol Acetates, Carbohydrate Research, 40 (1975) pp. 217-225, Elsevier Science Publishers.

Carpita, N., et al., Linkage Structure of Carbohydrates by Gas Chromatography-Mass Spectrometry (GC-MS) of Partially Methylated Alditol Acetates, Analysis of Carbohydrates by GLC and MS, pp. 157-216, Supplied by The British Library—"The World's Knowledge".

A Method for the Analysis of Sugars in Plant Cell-Wall Polysaccharides by Gas-Liquid Chromatography, Carbohydrate Research, 5, 1967, pp. 340-345.

International Search Report for PCT/GB2004/002815 dated Jul. 12, 2004.

English abstract for JP 05-146273A dated Jun. 15, 1996 listed above.

Hashimoto, H., et al., *Production of the Positional Isomers of α-Galactobiose by the Reverse Reaction of α -Galactosidase Candida guilliermondii H-404*, , Journal of Applied Glycoscience, vol. 48, No. 3, (2001), pp. 279-285.

Hashimoto, H., et al., *Candida guilliermondii H-404*, Journal of Applied Glycoscience, vol. 41, No. 2, (1994), pp. 143-150 (includes English abstract).

Blanchette, D., et al., α- *and* β-*Galactosidase properites of Bifidobacterium infantis*, Milchwissenschaft, vol. 47, No. 1, (1992), pp. 18-21.

P. Moller et al; "Intra- and Extracellular β-Galactosidases from *Bifidobacterium bifidum* and *B. infantis*: Molecular Cloning, Heterologous Expression, and Comparative Characterization", Applied and Environmental Microbiology, May 2001, pp. 2276-2283.

V. Dumortier et al, "Primary structure of ten galactosides formed by transglycosylation during lactose hydrolysis by *Bifidobacterium bifidum*"; Carbohydrate Research, 201 (1990), pp. 115-123.

J. Paton et al; "Pathogenesis and Diagnosis of Shiga Toxin-Producing *Escherichia coli* Infections"; Clinical Microbiology Reviews, Jul. 1998, pp. 450-479.

K. Karlsson; "Animal Glycosphingolipids as Membrane Attachment Sites for Bacteria"; Annu. Rev. Biochem, 1989, 58: pp. 309-350.

E. Olano-Martin et al; "Pectins and Pectic-oligosaccharides inhibit *Escherichia coli* O157:H7 Shiga toxin as directed towards the human colonic cell line HT29"; FEMS Microbiology Letters 218 (2003), pp. 101-105.

T. Sako et al; "Recent progress on research and applications of non-digestible galacto-oligosaccharides"; International Dairy Journal 9 (1999), pp. 69-80.

K. Van Laere et al; "Characterization of a Novel β-Galactosidase from *Bifidobacterium adolescentis* DSM 20083 Active towards Transgalactooligosaccharides", Applied and Environmental Microbiology, Apr. 2000, pp. 1379-1384.

S. Zarate et al; "Oligosaccharide Formation During Enzymatic Lactose Hydrolysis: A Literature Review"; Journal of Food Protection, vol. 53, No. 3, pp. 262-268 (Mar. 1990).

J.E. Prenosil et al; "Formation of Oligosaccharides during Enzymatic Lactose: Part 1: State of Art"; Biotechnology and Bioengineering, vol. 30, pp. 1019-1025 (1987).

M. Hung et al; "Molecular and Biochemical Analysis of Two β-Galactosidases from *Bifidobacterium infantis* HL96"; Applied and Environmental Microbiology, Sep. 2001, pp. 4256-4263.

N. Onishi et al; "Production of Galacto-Oligosaccharide from Lactose by *Sterigmatomyces elviae* CBS8119", Applied and Environmental Microbiology, Nov. 1995, pp. 4022-4025.

G. Gibson; "*Bifidobacteria* and Oligosaccharides-The Functional Use of Prebiotics"; Positive Nutrition: Functional Foods; IBC Technical Services, London 1995, 34 pages.

G. Gibson; "Prebiotics: New Developments in Functional Foods"; Chandos Publishing, Oxford 2000, 96 pages.

V. Dumortier et al; "Purification and properties of a β-D-galactosidase from *Bifidobacterium bifidum* exhibiting a transgalactosylation reaction"; Biotechnol. Appl. Biochem. 19, pp. 341-354 (1994).

B. Rabiu et al; "Synthesis and Fermentation Properties and Novel Galacto-Oligosaccharides by β-Galactosidases from *Bifidobacterium* Species"; Applied and Environmental Microbiology, Jun. 2001, pp. 2526-2530.

R. Crittenden; "Prebiotics"; Probiotics: A Critical Review ISBN 1-898486-15-8; 1999 Horizon Scientific Press, Wymondham, U.K., pp. 141-156.

R. Tanaka, et al; "Effects of Administration of TOS and *Bifidobacterium breve* 4006 on the Human Fecal Flora"; Bifidobacteria Microflora, vol. 2(1), 17-24, 1983.

M. Ito, et al.; Effects of Administration of Galactooligosaccharides on the Human Faecal Microflora, Stool Weight and Abdominal Sensation; Microbial Ecology in Health and Disease, vol. 3:285-292 (1990).

M. Ito, et al.; "Effects of Transgalactosylated Disaccharides on the Human Intestinal Microflora and Their Metabolism"; J. Nutr. Sci. Vitaminol., 39, 279-288, 1993.

Schell, et al., "*The genome sequence of Bifidobacterium longum reflects its adaptation to the human gastrointestinal tract*", Proceedings of the National Academy of Science, vol. 99, Oct. 29, 2009, pp. 14422-14427 (including PNAS Corrections, Jun. 28, 2005, pp. 9429-9430).

U.S. Office Action dated Sep. 8, 2010 for U.S. Appl. No. 12/225,626 noting Schell, et al. listed in this IDS.

Russel P., 2002 iGenetics, Pearson Education, Inc., San Francisco, pp. 187-189.

Lawson, Paul A. et al., "Recognition of *Fusobacterium nucleatum* subgroups Fn-1, Fn-2 and Fn-3 by ribosomal RNA gene restriction patterns", FEMS Microbiology Letters, 1989. vol. 65, pp. 41-46.

Krieg, P.A. et al., "In Vitro RNA Synthesis with SP6 RNA Polymerase", Methods in Enzymology. vol. 155, pp. 397-415, 1987.

Sambrook J., et al., Molecular Cloning: A Laboratory Manual, vol. 3, Third Edition, (2002), Chapter 15, Expression of Cloned Genes in *Escherichia coli*, pp. 15.1-15.65 www.MolecularCloning.com.

Chabaud, et al., "*Contribution of Interleukin 17 to Synovium Matrix Destruction in Rheumatoid Arthritis*", Cytokine, vol. 12, No. 7, Jul. 2000, pp. 1092-1099.

Palframan, et al., "*Carbohydrate Preferences of Bifidobacterium Species Isolated from the Human Gut*", Current Issues in Intestinal Microbiology, vol. 4, 2003, pp. 71-75.

Yuan, et al., "*Feruloyl oligosaccharides stimulate the growth of Bifidobacterium bifidum*", Anaerobe, vol. 11, 2005, pp. 225-229.

Hanatani, Mitsuya et al., "*Physical and Genetic Characterization of the Melibiose Operon and Identification of the Gene Products in Escherichia coli*"; The Journal of Biological Chemistry, Feb. 10, 1984, vol. 259, No. 3, pp. 1807-1812.

Database UniProt [Online], "*Alpha-galactosidase (EC 3.2.1.22)*", XP002431984 retrieved from EBI accession No. UNIPROT:Q9XCX2, Database accession No. Q9XCX2, see sequence, Nov. 1, 1999.

Database Geneseq [Online] Nov. 19, 2002, "*Bibidobacterium longum* NCC2705 ORF amino acid sequence SEQ ID No. 919." XP002431983 retrieved from EBI accession No. GSP:ABP66175; Database accession No.: ABP66175; see SEQ ID No. 919.

Lamoureux, et al., "Production of Oligosaccharides in Yogurt Containing *Bifidobacteria* and Yogurt Cultures", Journal of Dairy Science, American Dairy Science Association, Savoy, IL, US, vol. 85, No. 5, May 2002, pp. 1058-1069, XP001124200; ISSN:0022-0302 the whole document.

Van Laere, et al., Transglycosidase activity of *Bifidobacterium* adolescents DSM 20083 alpha-galactosidase, Applied Microbiology and Biotechnology, Springer Verlag, Berlin, DE, vol. 52, No. 5, Nov. 1999, pp. 681-688, XP002285615; ISSN:0175-7598 the whole document.

Scalabrini P. et al: "Characterization of *Bifidobacterium* Strains for Use in Soymilk Fermentation" International Journal of Food Microbiology, Elsevier Science Publishers, Amsterdam, NL, vol. 39, No. 3, 1998, pp. 213-219, XP000952364, ISSN: 0168-1605 the whole document, in particular Table 1.

Van Den Broek L A M et al: "Synthesis of alpha-galacto-oligosaccharides by a cloned alpha-galactosidase from *Bifidobacterium adolescentis*" Biotechnology Letters, vol. 21, No. 5, May 1999, pp.

441-445, XP009083120; ISSN: 0141-5492 the whole document, in particular p. 443, left-handed column, last paragraph.
Database EMBL (Online) Oct. 26, 2000, "*Bifidobacterium bifidum* gene for beta-galactosidase (3701 bp)" 3 pages, XP002429539.
Database UniProt (Online) Mar. 1, 2001, "Beta-galactosidase (EC 3.2.1.23)." 1 page XP002429540.
Smeianov et al., GenBAnk accession No. AAG02023, 2000.

Rowland et al., "*The effects of transgalactosylated oligosaccharides on gut flora metabolism in rats associated with a human faecal microflora*", Journal of Applied Bacteriology, 1993, 74, pp. 667-674.
Matsumoto et al., "*Galactooligosaccharides*", Japanese Technology Reviews, Section E, Chapter 5, vol. 2.3, 1993, pp. 90-94 (9 sheets).

\* cited by examiner

GALACTOOLIGOSACCHARIDE COMPOSITION AND THE PREPARATION THEREOF

CROSS-REFERENCE TO RELATED APPLICATION

This application is a National Phase Patent Application of International Application Number PCT/GB2004/002815, filed on Jun. 30, 2004, which claims priority of British Patent Application Number 0315266.7, filed on Jun. 30, 2003, British Patent Application Number 0325224.4, filed on Oct. 29, 2003, and British Patent Application Number 0405837.6, filed on Mar. 16, 2004.

The present invention relates to novel strains of *Bifidobacterium bifidum* that produce a novel galactosidase enzyme activity capable of converting lactose to a novel mixture of galactooligosaccharides. Galactooligosaccharides are non-digestible carbohydrates, which are resistant to mammalian gastrointestinal digestive enzymes but are fermented by specific colonic bacteria. The invention also relates to the use of a bifidobacterial strain to produce a novel galactooligosaccharide composition that is capable of promoting the growth of bifidobacteria in the gut. It also relates to the novel composition of the galactooligosaccharide products.

The human gut flora comprises pathogenic, benign and beneficial microbial genera. A predominance of the former can lead to intestinal disorders that can be both acute (e.g. gastroenteritis) and chronic (e.g. inflammatory bowel disease, irritable bowel syndrome and some intestinal cancers). Attempts have been made to influence the balance of the gut flora in favour of beneficial microorganisms, such as the bifidobacteria, by adding one or more such microbial strains to an appropriate food vehicle. Such a live microbial feed supplement is known as a probiotic. However, it is difficult to guarantee the survival of live bacteria in foods and also after digestion.

An alternative approach to dietary manipulation of the gut microflora is the use of a prebiotic, which is defined as a non-digestible food ingredient that beneficially affects the host by selectively stimulating the growth and/or activity of one or a limited number of bacteria in the colon, thereby resulting in an improvement in the health of the host.

The human large intestinal microflora is acquired at birth. The breast-fed infant has a preponderance of bifidobacteria, which easily out compete other genera. This is because human milk components are stimulatory. In contrast, the formula-fed infant has a more complex flora which resembles the adult gut in that bacteroides, clostridia, bifidobacteria, lactobacilli, gram positive cocci, coliforms and other groups are all represented in fairly equal proportions. Bifidobacteria are generally regarded as protective with regard to the large intestinal infections and this difference probably explains the much lower incidence of infection in breast fed infants compared to those who are fed on formula milk.

Certain components of the gut flora have been implicated in the aetiology of gut disease. For example, mycobacteria are associated with Crohn's disease, ulcerative colitis may be triggered by sulphate reducing bacteria and there may be bacterial involvement in the development of bowel cancer. It would clearly be of benefit if the selective growth of indigenous beneficial gut bacteria could be encouraged by the ingestion of a prebiotic. This would have the ongoing effect that the pathogenic microflora would be repressed.

One group of compounds that is classified as prebiotics is the galactooligosaccharides, which are galactose-containing oligosaccharides of the form Glc α1-4[βGal 1-6]$_n$ where n=2-5, and are produced from lactose syrup using the transgalactosylase activity of the enzyme β-galactosidase (Crittenden, (1999) Probiotics: A Critical Review. Tannock, G.(ed) Horizon Scientific Press, Wymondham, pp. 141-156). Three products are currently commercially available having slightly different compositions. The first of these, transgalactosylated oligosaccharides (TOS), is produced using β-galactosidase from *Aspergillus oryzae* (Tanaka et al, (1983) *Bifidobacteria Microflora*, 2, 17-24), and consists of tri-, tetra-, penta- and hexa-galacto-oligosaccharides. The second is Oligomate 55, which is prepared using β-galactosidase from *A. oryzae* and *Streptococcus thermophilus* (Ito et al., (1990), *Microbial Ecology in Health and Disease*, 3, 285-292) and contains 36% tri-, tetra-, penta- and hexa-galacto-oligosaccharides, 16% disaccharides galactosyl glucose and galactosyl galactose, 38% monosaccharides and 10% lactose. Finally, a transgalactosylated disaccharide (TD) preparation is produced using β-galactosidase from *S. thermophilus* (Ito et al., (1993), *J. Nutritional Science and Vitaminology*, 39, 279-288).

It is known that members of the bifidobacteria produce β-galactosidase enzymes that are involved in the bacterial metabolism of lactose. Moller, P. L. et al in *Appl. & Environ. Microbiol.*, (2001), 62, (5), 2276-2283 describe the isolation and characterization of three β-galactosidase genes from a strain of *Bifidobacterium bifidum*.

US Patent Publication No US 2002/0086358 describes a new β-galactosidase from *Bifidobacterium bifidum*, in particular a truncated version of the enzyme that has a high transgalactosylating activity. Whilst it was stated that incubation with lactose could take place in the presence of 0.5-60% lactose, the maximum exemplified yield of galactooligosaccharide produced in transgalactosylation reactions was 44% (mg of oligosaccharide produced per mg lactose added). Moreover, from the definition of oligosaccharide in this U.S. patent publication it is evident that the product consists of at least three linked sugar molecules.

Dumortier et al in *Carbohydrate Research*, 201, (1990), 115-123 describe the formation of oligosaccharides by a transgalactosylation reaction during lactose hydrolysis with *Bifidobacterium bifidum* DSM 20456. Their analysis of the structure of the mixture of oligosaccharides produced showed that the linkages were β-(1→3), β-(1→6) and β-(1→4)-D-galactosyl linkages. Dumortier suggests that compounds produced by *Bifidobacterium bifidum* are involved in the adherence of bacteria in the large intestine.

Strains of *bifidobacterium* have now been found that are not only capable of producing a galactosidase enzyme activity that converts lactose to a mixture of galactooligosaccharides, but also produce a galactooligosaccharide mixture which contains up to 35% of the disaccharide galabiose (Gal (α1-6)-Gal). The latter is known (see Paton, J. C. & Paton, A. W. (1989), *Clin. Microbiol. Revs.*, 11, 450-479; Carlsson, K. A. (1989), *Ann. Reviews Biochem.*, 58, 309-350.) to be an antiadhesive capable of preventing the adhesion of toxins, e.g. Shiga toxin, and pathogens, such as *E. coli*, to the wall of the gut.

Figure 1:
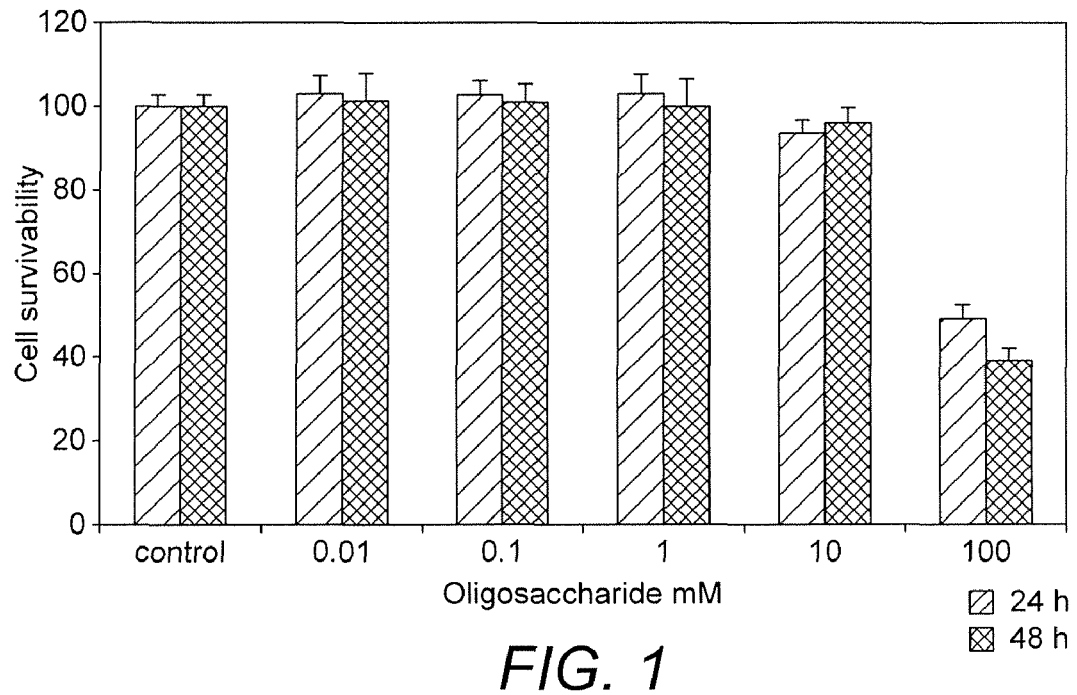
FIG. 1 is a chart of the cell survivability as affected by the addition of different oligosaccharide concentrations after 24 and 48 hours of incubation.

According to the invention there is provided a strain of *Bifidobacterium bifidum* capable of producing a galactosidase enzyme activity that converts lactose to a mixture of galactooligosaccharides comprising at least one disaccharide, at least one trisaccharide, at least one tetrasaccharide and at least one pentasaccharide. Preferably the mixture comprises from 20 to 35% w/v of the disaccharide, from 20 to 35% w/v of the trisaccharide, from 15 to 25% w/v of the tetrasaccharide and from 10 to 20% w/v of the pentasaccharide.

The term enzyme activity", as used in relation to the galactosidase enzyme activity of the present invention, is the activity resulting from at least one galactosidase enzyme.

In one aspect, the galactooligosaccharide mixture has been found to comprise the disaccharide Gal-Gal, the trisaccharide Gal-Gal-Glc, the tetrasaccharide Gal-Gal-Gal-Glc and the pentasaccharide Gal-Gal-Gal-Gal-Glc, where Gal represents a galactose residue and Glc represents a glucose residue.

Using methylation analysis and enzymatic hydrolysis the galactooligosaccharide mixture has been found to comprise Gal ($\beta$1-6)-Gal ($\beta$1-6)-Gal ($\beta$1-4)-Glc tetrasaccharide; Gal ($\beta$1-6)-Gal ($\beta$1-4)-Glc and Gal ($\beta$1-3)-Gal ($\beta$1-4)-Glc trisaccharides; Gal ($\beta$1-3)-Glc, Gal ($\beta$1-3)-Gal, Gal ($\beta$1-6)-Gal and Gal ($\alpha$1-6)-Gal disaccharides.

A strain of *Bifidobacterium bifidum* capable of producing a galactosidase enzyme activity that converts lactose to the mixture of galactooligosaccharides as defined above has been deposited under accession number NCIMB 41171 at the National Collection of Industrial and Marine Bacteria, Aberdeen on 31 Mar. 2003.

Such a deposited strain of *Bifidobacterium bifidum*, or its biologically functional equivalent, can be used to produce the galactooligosaccharide mixture as defined above. The mixture of galactooligosaccharides may form part of a product for improving gut health by promoting the growth of bifidobacteria in the gut, specifically the origin producer strain. Such a product may be selected from the group consisting of dairy products (for example, liquid milk, dried milk powder such as whole milk powder, skimmed milk powder, fat filled milk powders, whey powders, baby milks, ice cream, yoghurt, cheese, fermented dairy products), beverages, infant foods, cereals, bread, biscuits, confectionary, cakes, food supplements, dietary supplements, animal feeds, poultry feeds or indeed any other food or beverage.

The mixture of oligosaccharides may also be used for the preparation of a medicament for preventing the adhesion of pathogens or toxins produced by pathogens to the gut wall. The mixture may be administered to a patient following a course of antibiotic treatment, which often alters or even destroys the normal healthy gut flora, or following surgery on the gut, in order to "reseed" or re-establish in the gut the normal flora of a healthy gut. The mixture of galactooligosaccharides may be used in combination with the strain of *Bifidobacterium bifidum* referred to above or a biologically functional equivalent.

The phrase "biologically finctional equivalent" is construed to mean a strain of *Bifidobacterium bifidum* that is capable of producing a galactosidase enzyme activity that converts lactose into the mixture of galactooligosaccharides as defined above.

According to another aspect of the invention there is provided a galactooligosaccharide composition for promoting growth of bifidobacteria comprising as effective constituents at least one disaccharide, at least one trisaccharide, at least one tetrasaccharide and at least one pentasaccharide.

The galactooligosaccharide composition preferably comprises the galactooligosaccharide mixture as hereinbefore described.

Preferably the galactooligosacharide composition comprises from 20 to 35% w/v of the disaccharide, from 20 to 35% w/v of the trisaccharide(s), from 15 to 25% w/v of the tetrasaccharide and from 10 to 20% w/v of the pentasaccharide.

According to yet another aspect of the invention there is provided a method for the manufacture of a substance for promoting the growth of bifidobacteria characterised in that lactose or a lactose-containing material is treated with a strain of *Bifidobacterium bifidum* as defined above.

Suitable lactose-containing material may be selected from commercially available lactose, whole milk, semi-skimmed milk, skimmed milk, whey and fat-filled milk. Such milk products may be obtained from cows, buffalos, sheep or goats. Fat-filled milk is defined as whole milk that has been skimmed to remove the dairy fat, which is subsequently replaced by the addition of vegetable fat or oil.

Using growth media supplemented with carbohydrate substrates other than lactose it has been found that *Bifidobacterium bifidum* according to the invention can utilise maltose, raffinose, xylan and fructose. Culturing of the bacteria in medium supplemented with one of these carbohydrates induced the expression of $\alpha$-glucosidase, $\alpha$-galactosidase, xylosidase and $\beta$-fructofuranosidase respectively and thus resulted in the production of $\alpha$-glucooligosaccharides, $\alpha$-galactooligosaccharides, xylooligosaccharides and fructooligosaccharides respectively.

In an investigation leading to the present invention, gut derived bacteria were screened for those that were capable of producing galactosidase and thus had the highest potential for producing galactooligosaccharide(s). As a result, it has been found that certain bacteria belonging to the genus *Bifidobacterium*, in particular *Bifidobacterium bifidum*, were not only able to produce a galactosidase enzyme activity but also that the enzyme could convert lactose to a galactooligosaccharide mixture comprising from 20 to 35% w/v of a disaccharide, from 20 to 35% w/v of trisaccharide, from 15 to 25% w/v of a tetrasaccharide, from 10 to 20% w/v of a pentasaccharide. A specific example of *Bifidobacterium bifidum* was deposited on 31 Mar. 2003 with NCIMB, Aberdeen under accession number 41171.

In order to culture these bacteria, any nutrient source can be utilized provided it can be assimilated by the bacteria. Appropriate culture media can be formulated with, for example, carbohydrates such as lactose, sucrose or glucose; nitrogen containing inorganic or organic nutrient sources such as yeast extract, tryptone, meat extract (Lab Lemco) and the like; inorganic nutrient sources such as phosphates, potassium and the like. For culturing, the pH of the nutrient medium should be within the range of 6.0 to 8.0. preferably 7.0 and culturing is carried out anaerobically at a temperature range of from 35° to 40° C., preferably 37° C. for from 40 to 64 hours, preferably 50 hours.

The strain can be cultured by any of the known cultural methods such as stationary phase culture, anaerobic submerged culture or shake culture. The bacterial cells are harvested by centrifugation or filtration and the cells can be used as such as the reaction catalyst without further treatment. As an alternative the cells may be used in an immobilized state by an appropriate immobilization procedure.

The *Bifidobacterium bifidum* of the invention may be used to convert lactose itself or lactose contained in a milk product into the novel galactooligosaccharide composition of the invention. Following conversion the bacterial cells may be removed by centrifugation. Any monosaccharide present may be removed using, for example, incubation with the yeast *Saccharomyces cerevisiae*. The mixture may then subsequently be subjected to centrifugation and microfiltration. The resultant GOS solution may then be spray-dried to produce a powder.

Milk containing the galactooligosaccharide composition of the invention produced in this way may be administered directly to children, adults or animals. Alternatively, it may be used to produce products such as bread, confectionary or the like, where the stability of galactooligosaccharides under acidic and high temperature conditions enables it to be used without decomposition. Alternatively the GOS powder may be added to a product as listed above.

The GOS powder may be administered to patients suffering from such intestinal disorders as inflammatory bowel disease and irritable bowel syndrome, in which case the patient may ingest a daily dose of from 2 to 20 g, preferably 5 to 10 g, most preferably 7 g, taken in two separate doses.

Alternatively, the galactooligosaccharide composition of the invention may be mixed with a culture of the *Bifidobacterium bifidum* according to the invention to produce a mixture for improving gut health. Such a mixture is classed as a synbiotic, which is defined as 'a mixture of probiotic and prebiotic that beneficially affects the host by improving the survival and implantation of live microbial dietary supplement in the GI tract' (see Gibson and Roberfroid, 1995, Dietary modulation of the human microbiota: introducing the concept of prebiotics. Journal of Nutrition 125, 1401-1412). Such a combination enhances the survival of the probiotic in the hostile environment of the colon by offering an available selective substrate. The bacterial probiotic may be microencapsulated in the galactooligosaccharide prebiotic to produce, for example, a powder, which may then be added to dairy products, such as yoghurt, or used as a dietary supplement.

The advantage of ingesting milk or other products containing the galactooligosaccharide composition of the invention is it promotes an increase in the levels of beneficial bifidobacteria in the gut, at the expense of other less desirable bacteria present in the gut micoflora, such as the clostridia. Thus, there is a decrease in certain indigenous bacteria that could have a deleterious effect upon the health of the individual. This would then result in a reduction of gastrointestinal tract infections. It helps to prevent or treat colitis, shortens diarrhoeal incidents and reduces the risk of chronic gut diseases such as ulcerative colitis and cancer. It may also help to relieve the symptoms of irritable bowel syndrome.

Farm animals fed on a diet supplemented with the galactooligosaccharide composition of the invention in, for example, powder form, may show an improved weight conversion of their feed.

The present invention will be further described by way of reference to the following examples.

EXAMPLE 1

1l of medium (pH 7.0) containing 10.0 g/l tryptone. 5.0 g/l Lab-LEMCO (meat extract), 5.0 g/l yeast extract, 3.0 g/l K HPO, 0.05 g/l cysteine HCL, 10 g/l lactose and 1 ml/l Tween 80 was sterilized at 121° C. for 15 min. After sterilization the medium was inoculated with 1.0% (v/v) of a fresh *Bifidobacterium bifidum* NCIMB 41171 culture and incubated under anaerobic condition at 37° C. for 50 h. The bacterial cells were harvested by centrifugation (30000 g for 20 min). After being washed twice with phosphate buffer (0.02M. pH 7.0) the cells were ready to be used in oligosaccharide synthesis reactions.

The bacterial cells (40 units of β-galactosidase activity) were resuspended in 100 ml of phosphate buffer (0.02M. pH 7.0) containing 50 g of lactose. The reaction was allowed to proceed at 40° C. and after 7 h the mixture consisted of 35% (w/v) hydrolysis products (glucose, galactose), 37% (w/v) lactose and 18% (w/v) galactooligosaccharides with a degree of polymerisation between 2-5. After removing the bacterial cells by centrifugation (3000 g for 20 min), monosaccharides (glucose and galactose) were removed by incubation with the yeast *Saccharomyces cerevisiae*. The yeast was subsequently removed by centrifugation (10000 g for 10 min) and the mixture was then filtered through a 0.1 μm microfiltration filter in order to secure the microbiological quality of the product. The sugar solution was then spray-dried in order to obtain the powder form. Products were quantitatively analysed by high performance liquid chromatography using a Merck-Hitachi LaChrom system (Merck, Poole, Dorset, UK) equipped with an APEX Carbohydrate column (Jones Chromatography, Mid Glamorgan, UK) and a Merck-Hitachi LaChrom RI detector. 70% (v/v) acetonitrile was used as an eluent at 25° C. and a flow rate of 0.8 ml/min. The galactooligosaccharide mixture comprised of 25% Gal-Gal, 35% Gal-Gal-Glc, 24% Gal-Gal-Gal-Glc and 16% Gal-Gal-Gal-Gal-Glc.

EXAMPLE 2

*Bifidobacterium bifidum* NCIMB 41171 cells were prepared according to Example 1 and added to 500 ml of skimmed milk in a stirred tank, added (300 units of β-galactosidase activity). Lactose conversion was allowed to proceed at 40° C. After 8 h the galactooligosaccharides concentration was 22% (w/v) and the mixture comprised 28% Gal-Gal, 32% Gal-Gal-Glc, 21% Gal-Gal-Gal-Glc and 19% Gal-Gal-Gal-Gal-Glc.

EXAMPLE 3

In Vitro Gut Model

The conditions in the colon were replicated in a three stage continuous fermenter (Macfarlane et al., 1998, Microbial Ecology, 35, 180-187) inoculated with 10% (w/v) faecal homogenate from healthy human volunteers in a growth medium without and with 1% (w/v) the GOS mixture prepared according to Example 1 (Table 2). The model consisted of three vessels, V1, V2 and V3, with respective operating volumes of 270, 300 and 300 ml. Temperature was set at 37° C. and together with pH was controlled automatically. Culture pH in the three vessels was maintained at 5.5, 6.2 and 6.8, respectively. Each fermenter was magnetically stirred and kept under anaerobic conditions by continuously sparging with $O_2$-free $N_2$ (15 ml/min). The growth medium contained the following ingredients: starch 8 g/l, mucin 4 g/l, casein 3 g/l, peptone water 5 g/l, tryptone water 5 g/l, bile N°3 0.4 g/l, yeast, 4.5 g/l, $FeSO_4$ 0.005 g/l, NaCl 4.5 g/l, KCl 4.5 g/l, $KH_2PO_4$ 0.5 g/l, $MgSO_4.7H_2O$ 1.25 g/l, $CaCl_2.6H_2O$ 0.15 g/l, $NaHCO_3$ 1.5 g/l, Tween 80 1 ml, Hemin 0.05 g/l, Cysteine.HCl 0.8 g/l. The medium was fed to V1 by peristaltic pump and V1 sequentially supplied V2 and V3 through a series of tubes. The system was operated at a retention time of about 36 hours. The gut model was left overnight to equilibrate before the medium pump was switched on and was run for at least 10 days before medium containing testing substrate was introduced and it was then left for further 10 days. Samples were taken at the beginning and the end of each cycle. The sample volume removed was 5 ml and this amount was used for bacterial group enumeration.

Fluorescence In Situ Hybridisation (FISH)

Differences in bacterial populations were assessed through use of FISH with oligonucleotide probes designed to target diagnostic regions of 16S rRNA. These were commercially synthesised and labelled with the fluorescent dye Cy3 (provided by Eurogentec UK Ltd). The molecular probes utilised were presented in Table 1. For total bacterial counts the nucleic acid stain 4,6-diamidino-2-phenylindole (DAPI) was used. Samples obtained from fermentation vessels were diluted in 4% (w/v) paraformaldehyde and fixed overnight at 4° C. The cells were then centrifuged at 1500×g for 5 minutes, washed twice with phosphate-buffered saline (PBS; 0.1M, pH 7.0), resuspended in a mixture of PBS/99% ethanol (1:1 w/v) and stored at −20° C. for at least 1 hour. The cell suspension was then added to the hybridisation mixture and left overnight to hybridise at the appropriate temperature for each probe. Hybridised mixture was vacuum filtered using a 0.2 μm Isopore membrane filter (Millipore Corporation, Herts, UK). The filter was removed, placed onto a glass slide with SlowFade (Molecular Probes, Eugan, Oreg., USA) and examined under a fluorescent microscope (Nicon Eclipse, E400). The DAPI stained cells were examined under UV light and hybridised cells viewed using a DM510 filter. For each slide at least 15 different fields of view were counted.

TABLE 3

Bacterial populations as determined by FISH in an in vitro gut model when the synthesized GOS of the present invention was used as a substrate at 7 g per day.

|  | V1 | | | V2 | | | V3 | | |
| --- | --- | --- | --- | --- | --- | --- | --- | --- | --- |
| Time (days) | 1 | 10.5 | 21 | 1 | 10.5 | 21 | 1 | 10.5 | 21 |
| Total bacteria (log no.) | 9.4 | 9.7 | 9.6 | 9.4 | 9.5 | 9.6 | 9.6 | 9.5 | 9.5 |
| Bifidobacterium spp. | 8.1 | 8.0 | 8.9 | 8.0 | 8.0 | 8.7 | 8.2 | 8.2 | 8.4 |
| Lactobacillus spp | 7.4 | 7.6 | 7.6 | 7.3 | 7.3 | 7.5 | 7.4 | 7.3 | 7.3 |
| Bacteroides spp | 8.0 | 8.2 | 8.2 | 8.0 | 8.1 | 8.1 | 7.8 | 7.8 | 7.8 |
| Clostridium histolyticum group | 6.9 | 7.0 | 6.8 | 6.8 | 6.8 | 6.7 | 7.0 | 7.0 | 6.9 |

CONCLUSION

From Table 3, it can be seen that the GOS mixture of the present invention shows better prebiotic properties, (i.e. a higher increase in Bifidobacteria, as well as a decrease in bacteroides than the commercial GOS equivalent (see Table

TABLE 1

Oligonucleotide probes used for the characterisation of gut microflora using FISH

| Probe | Sequence | Target genus | Temperature | Reference |
| --- | --- | --- | --- | --- |
| Bac 303 | 5'-CCAATGTGGGGGACCTT-3' | Bacteroides spp. | 45° C. | Langendijk et al. (1995) |
| Bif 164 | 5'-CATCCGGCATTACCACCC-3' | Bifidobacterium spp. | 50° C. | Manz et al. (1996) |
| Chis 150 | 5'-AAAGGAAGAUUAAUACCGCAUA-3' | Clostridium histolyticum group | 50° C. | Franks et al. (1998) |
| Lab 158 | 5'-GGTATTAGCA(T/C)CTGTTTCCA-3' | Lactobacillus/ Enterococcus spp. | 45° C. | Harmsen et al. (1999) |

Results

TABLE 2

Bacterial populations as determined by FISH in an in vitro gut model when commercial GOS (Vivinal (RTM)) was used as a substrate at 7 g per day.

|  | V1 | | | V2 | | | V3 | | |
| --- | --- | --- | --- | --- | --- | --- | --- | --- | --- |
| Time (days) | 1 | 10.5 | 21 | 1 | 10.5 | 21 | 1 | 10.5 | 21 |
| Total bacteria (log no.) | 9.5 | 9.5 | 9.6 | 9.5 | 9.4 | 9.5 | 9.5 | 9.4 | 9.6 |
| Bifidobacterium spp. | 8.0 | 7.9 | 8.3 | 8.0 | 8.0 | 8.3 | 8.0 | 8.0 | 8.2 |
| Lactobacillus spp | 7.2 | 7.2 | 7.1 | 7.0 | 7.0 | 7.1 | 7.0 | 7.0 | 6.9 |
| Bacteroides spp | 8.1 | 8.1 | 7.5 | 8.0 | 8.2 | 7.5 | 8.0 | 8.1 | 7.9 |
| Clostridium histolyticum group | 6.8 | 6.9 | 7.1 | 6.9 | 6.8 | 7.0 | 6.9 | 6.8 | 7.0 |

2). The prebiotic effect was stronger in vessel 1 (V1) and 2 (V2), which is explained by the fact that GOS of the present invention consists of low molecular weight oligosaccharides.

EXAMPLE 4

Methylation Analysis

Galactooligosaccharide synthesis products prepared according to Example 1 were purified by gel filtration on a column of Biogel P2 (Pharmacia) eluted at 3 ml min$^{-1}$ with water.

Linkage positions for the respective galacto-oligosaccharides preparations were determined by methylation analysis. The freeze-dried samples (5-6 mg) were dispersed in dry dimethyl-sulfoxide (DMSO) at 20° C. for 16 h after flushing with argon. They were methylated by sequential addition of powdered sodium hydroxide (0.5 g) and iodomethane (4 ml) (Ciucanu and Kerek, 1984; MacCormick et al, 1993). After elution-extraction on a C18-bonded cartridge (Sep-Pak, Waters, Watford, UK), the methylated carbohydrates were dried, extracted into $CHCl_3/CH_3OH$ (1:1, v:v), and evaporated to dryness. The samples were hydrolysed using trifluoroacetic acid (Blakeney et al, 1983), and converted to partially methylated alditol acetates (PMAAs) by $NaBD_4$ reduction and acetylation with acetic anhydride and N-methylimidazole (Alberscheim et al, 1967).

The PMAAs were analysed by GC on a cross-bonded 50% cyanopropyl methyl-50% phenyl methyl polysiloxane column (Thames Chromatrography, Maidenhead, UK) using a flame ionisation detector and a temperature program: 55° C. (2 min), +45° C. $min^{-1}$ (1.9 min), 140° C. (2 min), +2° C. $min^{-1}$ (35 min), 210° C. (40 min). The PMAAs were identified by measuring their retention times relative to myo-inositol hexaacetate, and comparing the relative retention times with those of external standards. A mixture of standards for each sugar was prepared by deliberate methylation of methyl glycosides (Doares et al, 1991). Peak areas were represented as relative molar quantities using effective carbon response factors (Sweet et al, 1975).

Identities of PMAAs were confirmed by their electron-ionisation mass spectra (Carpita and Shia, 1989). GC-MS analysis was performed on an identical GC in series with a Fisons Analytical Trio 1S mass spectrometer, using a source temperature of 200° C. and an ionization potential of 70 eV.

In order to determine the anomeric configuration of the synthesis product, the oligosaccharides were treated with α-Galactosidase or β-Galactosidase (Melibiase; Sigma) at the optimum conditions suggested for 30 min. The reaction products were analysed by HPLC.

Results

From the above analysis the oligosaccharide structure was estimated to be for the tetrasaccharide fraction Gal (β1-6)-Gal (β1-6)-Gal (β1-4)-Glc, the trisaccharide fraction Gal (β1-6)-Gal (β1-4)-Glc; Gal (β1-3)-Gal (β1-4)-Glc and the disaccharide fraction Gal (β1-4)-Glc (lactose substrate); Gal (β1-3)-Glc; Gal (β1-3)-Gal; Gal (β1-6)-Gal; Gal (α1-6)-Gal (galabiose)

Gal: galactose, Glc: glucose

REFERENCES

1. Albersheim P. D., D. J. Nevins, P. D. English, and A. Karr. 1967. A method for the analysis of sugars on plant cell-wall polysaccharides by gas-liquid chromatography. Carbohydr Res 5: 340-345
2. Blakeney A. B., P. J. Harris, R. J. Henry and B. A. Stone. 1983. A simple and rapid preparation of alditol acetates for monosaccharide analysis. Carbohydr Res 113: 291-299
3. Carpita N. C., and E. M. Shia. 1989. Linkage structure of carbohydrates by gas chromatography-mass spectroscopy (GC-MS) for partially methylated alditol acetates, p. 157-216. In C. J. Biermann and G. D. McGinnis (ed.), Analysis of carbohydrates by gas-liquid chromatography and mass spectroscopy. CRC Press Poca Raton, Fla.
4. Ciucanu I., and F. Kerek. 1984. A simple and rapid method for the permethylation of carbohydrates. Carbohydr Res 131: 209-217
5. Doares S. H., P. Albersheim, and A. G. Darvill. 1991. An improved method for the preparation of standards for the glycosyl-linkage analysis of complex carbohydrates. Carbohydr Res 210: 311-317
6. MacCormick C. A., J. E. Harris, A. P. Cunning, and V. J. Morris. 1993. Characterization of a variant of polysaccharide acetan produced by a mutan of *Acetobacter xylinum*-strain CR 1/4. J Appl Bacteriol 74: 196-199
7. Sweet D. P., R Shapiro, and P. Albersheim. 1975. Quantitative analysis by various GLC response-factor theories for partially methylated and partially ethylated alditol acetates. Carbohydr Res 40: 217-225

EXAMPLE 5

Materials and Methods

The HT29 cell line was obtained from European Collection of Cell Cultures for Applied Microbiology and Research. Cell stocks were cultured at 37° C. in humidified 5% $CO_2$ in a standard mediurn containing high glucose Dulbecco's modified Eagle's medium (DMEM) supplemented with 5% (v/v) foetal bovine serum (FBS), 100 mM penicilin, 0.1M streptomycin, non essential amino acids (NEAA×100) and 200 mM a-glutamine. Cells were re-fed every 48 h and passaged before confluence was reached.

Oligosaccharide Sensitivity Assay

Serum standard medium (1% v/v) supplemented with different concentrations of oligosaccharides (0.01, 0.1, 1, 10, 100 mM) were used for oligosaccharide sensitivity assay according to Olano-Martin et al., 2003). Cells were re-fed experimental medium (containing the oligosaccharide of interest) daily, and measurement of adherent cells was performed by removal of experimental media and washing off the cells with $Ca^{++}$ free phosphate buffered saline (pH 7, 9.6 $gL^{-1}$). Adherent cells were then trypsinised and neutralised with an equal volume of serum standard medium. The cell suspension was diluted in Isoton II and cells were counted in a Coulter Counter. Percentage of cell survival was calculated as follow (FIG. 1)

% survival=(mean absorbance of treated cells/mean absorbance of control)×100

Adhesion Assay

HT29 cell were grown in 12-well tissue culture plates to >90% confluence using standard medium. For the last cell feeding prior to performing the assay, antibiotic-free medium was used.

Pathogens were grown anaerobically in antibiotic free cell culture medium for at least three subcultures. On the day of the assay, fresh pre-reduced tissue culture medium was inoculated with 10% of an overnight pathogen culture and incubated for 4 h prior to the assay.

Stock solution of the test oligosaccharides was prepared at a concentration of 5M in phosphate buffer saline and filter sterilised.

A 1/1000 dilution of the 4 h pathogen culture, was prepared in PBS and enumerated by plate counting. The medium was apirated off from the tissue culture plate and the cells were washed once in PBS (1 ml).

For each test oligosaccharide, 0.5 ml oligosaccharide (5M) solution was added to three wells. Phospate buffer saline (PBS) without any oligosaccharide was included as control. 0.5 ml of culture suspension was added to all wells, the plate was rock mixed and incubated aerobically at 37° C. for 2 h.

The culture was aspirated off, and all wells were washed three times in sterile PBS (1 ml per well). After the final washing, PBS was aspirated off and 70 µl trypsin/EDTA solution was added to each well, mixed and let stand for 5 minutes at 37° C.

1 ml PBS was added per well and pipette mixed to ensure that all the cells were removed from the bottom of the well and that clumps were broken up.

1 ml of the cell suspension was pipetted into a universal bottle of MRD (Maximum Recovery Diluent) and further diluted as appropriate. Dilutions were plated out on plate count agar (PCA) and incubated at 37° C. for 24 h.

Figure 2:
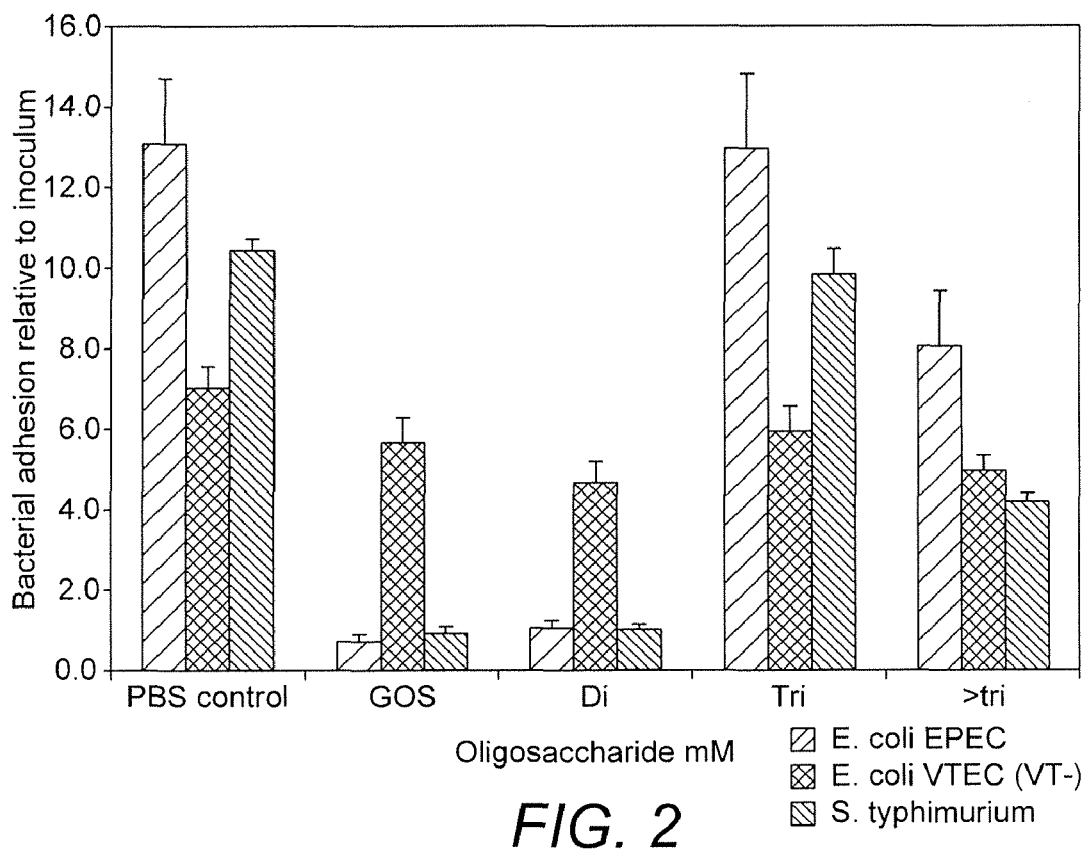
FIG. 2 is a chart of the effect of an oligosaccharide mixture and the different fractions of the mixture on the adhesion of *E. coli* EPEC, *E. coli* VTEC and *Salmonella typhimurium* to HT29 cells.

After incubation colonies were enumerated and inhibition of adhesion was calculated as the ratio of bacteria (c.f.u $ml^{-1}$) present in the sample to control (PBS) (FIG. 2).

CONCLUSION

The results shown in FIG. 2 indicate a strong inhibition of adhesion of *E. coli* EPEC and *S. typhimurium* in the presence of the disaccharide fraction, which inhibition is also present in the GOS mixture. There is a lower anti-adhesion effect in the presence of the higher than trisaccharide (>tri) fraction of the mixture against *S. typhimurium*.

The oligosaccharide sensitivity assay is performed to assure that are oligosaccharide mixture is not toxic to the HT29 cells (FIG. 1).

REFERENCES

Olano-Martin E., Williams M. R., Gibson G. R., Rastall R. A. 2003. Pectins and pectic-oligosaccharides inhibit *Escherichia coli* O157: H7 Shiga toxin as directed towards the human colonic cell line HT29. FEMS Microbiol Letters 218 (1): 101-105

EXAMPLE 6

The GOS product used in this examination was manufactured as previously described (Example 1) and inulin was obtained from Orafti (Belgium).

Forty weaned entire male pigs were purchased from JSR Genetics Ltd. Southburn, Driffield, Yorkshire. YO25 9ED On arrival at Reading University pigs were group housed in four groups of ten pigs for a period of seven days to allow pigs time to settle following transport and acclimatise to the unit and diet. The average weight of pigs at delivery was 14.70 kg.

Following a seven-day acclimatisation period the pigs were transferred to individual penning, within the same unit. The average weight of pigs at individual penning was 17.46 kg.

Pigs were identified by a unique ear tattoo, they were also individually numbered using a waterproof stock marker. Each individual pen was numbered with the same identification number as used to mark each pig.

Ten pigs were assigned to one of four diets, a control diet (NEG), diet supplemented with 1.6% (w/w) GOS prepared according to Example 1 to the control diet, diet supplemented with 4% (w/w) GOS to the control diet or diet supplemented with 1.6% (w/w) inulin to the control diet.

Pigs were bedded on sawdust throughout the study, straw was also provided as an environmental enrichment as were toys to help alleviate boredom.

Throughout the study pigs received Deltawean 15 NGP pellets (ABN, ABN House, PO Box 250, Oundle Rd, Woodston, Peterborough. PE 9QF) a complete feeding stuff for feeding ad-libitum to growing pigs.

Nutrient/mineral composition of Deltawean 15 NGP

| Nutrient | Inclusion |
| --- | --- |
| Oil | 3.3% |
| Protein | 19.2% |
| Fibre | 2.8% |
| Ash | 4.8% |
| Moisture | 13.8% |
| Vitamin A | 9500 i.u./kg |
| Vitamin E, alpha tocopherol | 100 i.u./kg |
| Vitamin D3 | 1850 i.u./kg |
| Selenium, sodium selenite | 0.30 mg/kg |
| Lysine | 1.32% |
| Copper, cupric sulphate | 170 mg/kg |

Pig feed also contained permitted antioxidants, Butylated hydroxyanisole (BHA), Butylated hydroxytoluene (BHT) and Ethoxyquin.

Pigs were allocated randomly to treatment although two or three pigs on the same dietary treatment were individually housed within the same group pen area. Pigs were grouped in this way to avoid the confounding of treatments should pigs escape from the individual pen, ie could only steal food containing the correct diet treatment for that particular pig. Individually housed pigs, in groups of two or three, on the same treatment, were allocated randomly throughout the unit.

Faecal samples were collected from each pig at the beginning and after four weeks of feeding the test diets, and faecal microbial populations were determined using FISH (Table 4) as previously described (Example 3). At the end of experiment, pigs were slaughtered to obtain proximal and distal colon contents samples. pH value (Table 5), short chain fatty acids (SCFA) (Table 6) and microbial populations (Table 7) were determined in the proximal and distal colon contents. Data are shown as mean±standard deviation. The differences were analysed by Student's t-test. Differences were considered significant at $P<0.05$.

TABLE 4

Effect of prebiotic treatment and diet on microbial population in faeces from pigs at the beginning and after four weeks experimental period

| | | Time 4 weeks | | | |
| --- | --- | --- | --- | --- | --- |
| | Time 0* | NEG[†] | 1.6% GOS[†] | 4% GOS[†] | Inulin[†] |
| Total Bacteria | 8.75 ± 0.22 | 8.97 ± 0.24 | 8.99 ± 0.23 | 8.97 ± 0.28 | 8.95 ± 0.28 |
| *Bifidobacterium* spp. | 6.48 ± 0.29 | 6.91 ± 0.25[o] | 7.07 ± 0.23[o] | 7.34 ± 0.21[a,o] | 7.45 ± 0.24[a,b,o] |
| *Lactobacillus* spp. | 6.33 ± 0.25 | 6.55 ± 0.23 | 6.93 ± 0.16[o] | 7.17 ± 0.24[a,o] | 6.94 ± 0.26[a,o] |
| *Bacteroides* spp. | 7.27 ± 0.23 | 7.75 ± 0.24[o] | 7.84 ± 0.27[o] | 7.85 ± 0.22[o] | 8.04 ± 0.18[o] |
| *Clostridium histolyticum* group | 7.43 ± 0.33 | 8.04 ± 0.24[o] | 8.14 ± 0.25[o] | 8.33 ± 0.28[o] | 8.22 ± 0.23[o] | cfu $log_{10}$/g of faeces; Each value is the mean ± SD,
*n = 40,
[†]n = 10; the differences were analysed by Student's t-test. Means in a row with superscripts significant different (P < 0.05)
[a]from NEG,
[b]from GOS 1.6%,
[o]from time 0.

TABLE 5

Effect of prebiotic treatment and diet on proximal and distal colon samples pH.

|  | NEG | 1.6% GOS | 4% GOS | Inulin |
|---|---|---|---|---|
| Proximal colon | 5.71 ± 0.16 | 5.65 ± 0.11 | 5.49 ± 0.14$^{a,b,c}$ | 5.90 ± 0.27 |
| Distal colon | 7.16 ± 0.04 | 7.16 ± 0.03 | 7.16 ± 0.04 | 7.12 ± 0.02 |

Each value is the mean ± SD, n = 10. The differences were analysed by Student's t-test. Means in a row with superscripts significant different (P < 0.05)
$^a$from NEG,
$^b$from GOS 1.6%,
$^c$from inulin.

TABLE 6

Effect of prebiotic treatment and diet on the proximal and distal colon samples SCFA concentrations*.

| | Proximal colon | | | | Distal colon | | | |
|---|---|---|---|---|---|---|---|---|
| | NEG | 1.6% GOS | 4% GOS | Inulin | NEG | 1.6% GOS | 4% GOS | Inulin |
| Lactic acid | 2.62 ± 0.73 | 6.62 ± 1.67$^a$ | 4.41 ± 0.77$^{a,b}$ | 3.07 ± 1.12$^b$ | ND | ND | ND | ND |
| Acetic acid | 41.43 ± 6.53 | 44.45 ± 2.81 | 51.85 ± 2.68$^{a,b,c}$ | 44.58 ± 3.31 | 31.61 ± 5.50 | 30.68 ± 2.32 | 33.57 ± 2.21 | 38.54 ± 3.66$^{a,b,c}$ |
| Propionic acid | 35.68 ± 5.1 | 27.52 ± 2.87$^a$ | 32.99 ± 8.39 | 30.63 ± 3.61 | 15.36 ± 3.46 | 15.27 ± 1.92 | 16.75 ± 3.88 | 17.36 ± 2.16 |
| Butyric acid | 10.51 ± 1.42 | 10.57 ± 1.56 | 11.19 ± 3.24 | 10.86 ± 3.99 | 4.81 ± 1.18 | 4.48 ± 0.73 | 5.13 ± 1.09 | 6.11 ± 1.42 |

Each value is the mean ± SD, n = 10. The differences were analysed by Student's t-test. Means in a row with superscripts significant different (P < 0.05)
$^a$from NEG,
$^b$from GOS 1.6%,
$^c$from inulin.
ND not detected;
*μmol/g on wet matter basis.

TABLE 7

Effect of prebiotic treatment and diet on microbial population in proximal and distal colon samples.

| | Proximal colon | | | | Distal colon | | | |
|---|---|---|---|---|---|---|---|---|
| | NEG | 1.6% GOS | 4% GOS | Inulin | NEG | 1.6% GOS | 4% GOS | Inulin |
| Total Bacteria | 8.61 ± 0.24 | 8.68 ± 0.22 | 8.62 ± 0.21 | 8.67 ± 0.25 | 8.83 ± 0.28 | 8.81 ± 0.21 | 8.80 ± 0.22 | 8.80 ± 0.29 |
| Bifidobacterium spp. | 7.13 ± 0.25 | 7.30 ± 0.26 | 7.87 ± 0.26$^{a,b,c}$ | 7.37 ± 0.32 | 7.03 ± 0.25 | 7.05 ± 0.26 | 7.41 ± 0.27$^a$ | 7.58 ± 0.32$^{a,b}$ |
| Lactobacillus spp. | 6.94 ± 0.23 | 7.17 ± 0.26 | 7.38 ± 0.24$^a$ | 7.19 ± 0.24 | 6.60 ± 0.34 | 6.96 ± 0.21 | 7.16 ± 0.35$^a$ | 7.05 ± 0.30 |
| Bacteroides spp. | 7.57 ± 0.21 | 7.76 ± 0.21 | 7.65 ± 0.33 | 7.97 ± 0.24$^a$ | 7.77 ± 0.27 | 7.88 ± 0.24 | 7.82 ± 0.26 | 8.04 ± 0.32 |
| Clostridium histolyticum group | 8.12 ± 0.23 | 8.08 ± 0.25 | 8.13 ± 0.28 | 8.07 ± 0.27 | 8.05 ± 0.41 | 8.15 ± 0.15 | 8.29 ± 0.19 | 8.18 ± 0.23 | cfu log$_{10}$/g on a wet basis; Each value is the mean ± SD, n = 10; the differences were analysed by Student's t-test. Means in a row with superscripts significant different (P < 0.05)
$^a$from NEG,
$^b$from GOS 1.6%,
$^c$from inulin.

CONCLUSION

Table 5: there is a drop in the proximal colon pH in the presence of GOS (for 1.6% and especially for 4%) which in combination with the SCFA data (Table 6) suggest that the GOS product reaches the proximal colon (fermentation products have increased)

Table 7: the presence of GOS (4%) shows a significant increase in the population numbers of beneficial bacteria (bifidobacteria, lactobacilli) in the proximal colon. This increase in the population numbers is lower in the distal part and in the faecal samples, which can be explained by the fact that the GOS product seems to be fermented mainly in the proximal colon. The 1.6% GOS treatment showed similar trends.

In the proximal colon an increase in the bifidobacterial population number can be seen as well as an increase in the production of acetic acid (main fermentation product of bifidobacteria). This suggests that the GOS product is very selective towards bifidobacteria species.

EXAMPLE 7

Case Studies

Case Study 1—Inflammatory Bowel Disease (IBD)

A 43 year old female patient with diagnosed ulcerative colitis (one of 2 major forms of IBD) is cited as a case study on the effects of the GOS product, prepared according to Example 1

The patient had suffered from ulcerative colitis for 5 years and was free of medication prior to, and during, the test period. The anti-inflammatory agent sulphasalazine had been used previously, but with no positive effect. The patient had difficulty in digesting foods, was on a standard diet, suffered from nausea, diarrhoea and abdominal pain. The latter was left side large intestine, which correlated with the diagnosis of colitis based inflammation of the descending colon.

A total daily GOS dose of 7 g/d (in 2 separate doses) was ingested. Within 4 days of intake, symptoms began to improve. The patient was better able to digest her diet, gut pains began to recede and nausea was reduced. There was no clinical analysis by endoscopy, but nevertheless the patient's feeling of well-being was markedly improved. The only change to the diet was the addition of GOS. Six weeks later, this effect has been maintained.

Whilst not a placebo controlled, multiple patient study, this case study provides anecdotal evidence for the positive effects of prebiotic GOS in one major form of IBD.

Case Study 2—Irritable Bowel Syndrome (IBS)

A 27 year old male who had suffered from IBS for 3 years has for 3 weeks been ingesting 7 g/d GOS prepared according to Example 1 in two separate doses. Prior to this period he experienced bloating, constipation, gut pain and tiredness. These are classical symptoms associated with IBS. The patient had not ingested antibiotics for 6 months and was on a wheat/gluten and sugar free diet.

Following the prebiotic intake, marked relief of these symptoms occurred within 3 days and has been maintained. The subject reports a dramatic improvement in overall well-being and gut health viz: "I am now ready to run a marathon". He is able to ingest a normal diet with no difficulties.

This report is not a controlled trial but does act as anecdotal evidence showing that GOS may improve the IBS condition and restore the sufferer to a better quality of life.

The invention claimed is:

1. A strain of *Bifidobacterium bifidum* having accession no. NCIMB 41171 capable of producing a galactosidase enzyme activity that converts lactose to a galactooligosaccharide mixture comprising disaccharide Gal (α1-6)-Gal, at least one trisaccharide selected from the group consisting of Gal (β1-6)-Gal(β1-4)-Glc and Gal(β1-3)-Gal(β1-4)-Glc, tetrasaccharide Gal (β1-6)-Gal(β1-6)-Gal(β1-4)-Glc and pentasaccharide Gal (β1-6)-Gal(β1-6)-Gal (β1-6)-Gal(β1-4)-Glc.

2. The strain according to claim 1, wherein the galactooligosaccharide mixture comprises from 20 to 35% w/v of the disaccharide, from 20 to 35% w/v of the at least one trisaccharide, from 15 to 25% w/v of the tetrasaccharide and from 10 to 20% w/v of the pentasaccharide.

3. A galactooligosaccharide composition for promoting specific growth of bifidobacteria comprising, as effective constituents, a galactooligosaccharide mixture comprising disaccharide Gal(α1-6)-Gal, at least one trisaccharide selected from the group consisting of Gal (β1-6)-Gal(β1-4)-Glc and Gal (β1-3)-Gal (β1-4)-Glc, tetrasaccharide Gal (β1-6)-Gal(β1-6)-Gal(β1-4)-Glc and pentasaccharide Gal (β1-6)-Gal(β1-6)-Gal (β1-6) -Gal(β1-4)-Glc.

4. The galactooligosaccharide composition according to claim 3, comprising from 20 to 35% w/v of the disaccharide, from 20-35% w/v of the at least one trisaccharide, from 15-25% w/v of the tetrasaccharide and from 10-20% w/v of the pentasaccharide.

5. A composition for improving gut health comprising the galactooligosaccharide composition of claim 3 and a culture of a strain of *Bifidobacterium bifidum* capable of producing a galactosidase enzyme activity that converts lactose to the galactooligosaccharide mixture.

6. A method for preventing adhesion of pathogens or toxins produced by pathogens to the gut wall, comprising:
administering an effective amount of the galactooligosaccharide composition of claim 3.

7. A method for re-establishing a normal gut flora following antibiotic treatment or surgery, comprising:
administering an effective amount of the galactooligosaccharide composition of claim 3.

8. The method of claim 7, wherein the galactooligosaccharide composition is combined with a culture of strain NCIMB 41171 from *Bifidobacterium bifidum*.

9. A product for improving gut health comprising the galactooligosaccharide composition of claim 3.

10. The product for improving gut health of claim 9, further comprising a food or beverage selected from the group consisting of dairy products, beverages, infant foods, cereals, bread, biscuits, confectionary, cakes, food supplements, dietary supplements, animal feeds, poultry feeds, and combinations thereof, or any other food or beverage.

11. The product of claim 9, further comprising a culture of strain NCIMB 41171 from *Bifidobacterium bifidum*.

12. A method for the manufacture of a substance for promoting the growth of bifidobacteria comprising:
treating lactose or a lactose-containing material with cells from the strain of *Bifidobacterium bifidum* of claim 1; and
removing the cells from the treated lactose or lactose-containing material.

13. The method according to claim 12, wherein the lactose or the lactose-containing material is selected from the group consisting of commercially-available lactose, whole milk, semi-skimmed milk, skimmed milk, whey and fat-filled milk.

14. The method according to claim 13, wherein the milk is obtained from cattle, buffalos, sheep or goats.

15. The method according to claim 12, wherein following removal of the *Bifidobacterium bifidum* cells, the substance is spray-dried to produce a powder.

16. A method for treating inflammatory bowel disease or irritable bowel syndrome, comprising: administering an effective amount of the galactooligosaccharide composition of claim 3.

* * * * *

```
                        SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Bac 303 FISH probe

<400> SEQUENCE: 1
ccaatgtggg ggacctt                                                        17

<210> SEQ ID NO 2
<211> LENGTH: 18
<212> TYPE: DNA
<213> ORGANISM: Artificial Sequence
<220> FEATURE:
<223> OTHER INFORMATION: Bif 164 FISH probe

<400> SEQUENCE: 2
catccggcat taccaccc                                                       18

<210> SEQ ID NO 3
<211> LENGTH: 22
<212> TYPE: RNA
<213> ORGANISM: Artificial Sequence
<220> FEATURE:
<223> OTHER INFORMATION: Chis 150 FISH probe

<400> SEQUENCE: 3
aaaggaagau uaauaccgca ua                                                  22

<210> SEQ ID NO 4
<211> LENGTH: 20
<212> TYPE: DNA
<213> ORGANISM: Artificial Sequence
<220> FEATURE:
<223> OTHER INFORMATION: Lab 158 FISH probe
<220> FEATURE:
<221> NAME/KEY: misc_feature
<222> LOCATION: (11)..(11)
<223> OTHER INFORMATION: n = t or c

<400> SEQUENCE: 4
ggtattagca nctgtttcca                                                     20
```